United States Patent [19]
Schroeder et al.

[11] Patent Number: 5,516,534
[45] Date of Patent: May 14, 1996

[54] COMPOSITION AND METHOD FOR REDUCING STRUCTURAL DEFECTS

[75] Inventors: John Schroeder, Schenectady; Gillray L. Kandel, Troy, both of N.Y.

[73] Assignee: Rensselaer Polytechnic Institute, Troy, N.Y.

[21] Appl. No.: 158,024

[22] Filed: Nov. 26, 1993

[51] Int. Cl.⁶ ............................ A61K 33/43; A61K 33/14
[52] U.S. Cl. ......................... 424/602; 424/610; 424/663; 424/673; 514/912
[58] Field of Search .................................... 424/602, 610, 424/663, 673; 514/912

[56] References Cited

PUBLICATIONS

Schreiber et al. "Lithium Administered by Eye Drops: A Better Treatment . . . " *Prog. Neuro–Psychopharmacol. & Biol. Psychiat.* 15, 315–321 (1991).

Kobayashi et al. "Effect of 2,6–diiodo–4–nitrophenol and 3,5–diiodosalicylic acid . . . " *Atarashii Ganka* 4(3), 403–6 (1987).

Iwata et al. "Cations involved in cataract formation. I. The turbidimetric aspect . . . " *Nippon Ganka Kiyo* 29(6), 855–58 (1978).

Bentley et al. "Effects of Lithium on Ionic Composition and Electrical . . . " *Exp. Eye Res.* 25, 447–457 (1977).

Farkash et al. "Pupillary Mydriasis Found to be Exerted Through $M_3$ Muscarinic . . . " *Lithium* 4, 279–283 (1993).

*Primary Examiner*—Zohreh Fay
*Attorney, Agent, or Firm*—Heslin & Rothenberg

[57] ABSTRACT

The invention provides a composition and method for reducing structural defects in metastable systems. Structural defects represent spaces or vacancies in the structural order of the metastable system, which can be restored to the predefect order through the use of structure makers. These structure makers will then occupy the space or vacancy of the defect, restoring the order of the system. Lithium ions are used as a preferred structure maker to reduce the structural defects that lead to cataract in a human lens.

4 Claims, 2 Drawing Sheets

COMPOSITION AND METHOD FOR REDUCING STRUCTURAL DEFECTS

FIELD OF THE INVENTION

This invention relates in general to a composition and method for reducing structural changes (defects) and preventing their subsequent effects in metastable biological systems, and more particularly to the use of structure makers such as lithium ions, and salts thereof, to reduce and/or prevent cataract formation in the human crystalline lens.

BACKGROUND OF THE INVENTION

Age is a significant risk factor in cataract formation. Such cataracts that develop in the elderly are referred to as senile cataracts. Cataracts can also be caused by trauma or as by-products of disease, or be congenital in nature. Cataracts are also thought to result from the use of certain drugs, such as alcohol [see J. J. Harding and R. Van Heyningen, British Journal of Ophthalmology 72:809–814 (1988)], phenothiazine drugs and haloperidol [see N. E. Isaac et al., Arch Ophthalmol 109:256–260 (1991)], and allopurinol [see W. K. Clair et al., British Journal of Ophthalmology 73:173–176 (1989)].

In any type of cataract, the opacification (a molecular process of devitrification) of the crystalline lens is the chief cause of the visual loss in individuals with this condition. It is therefore desirable to find a method of reducing and/or preventing cataracts. Certain drugs are thought to have a protective or beneficial effect on the development of cataracts, such as aspirin, aspirin-like analgesics (paracetamol, ibuprofen), and cyclopenthiazide (a diuretic). See J. J. Harding et al., Acta Ophthalmologica 67:518–524 (1989); J. J. Harding and R. Van Heyningen, British Journal of Ophthalmology 2:809–814 (1988); J. M. Seddon et al., Arch Ophthalmol 109:252–255 (1991); B. E. K. Klein et al., Diabetes Care 10:495–499 (1987); and H. Cheng, British Journal of Ophthalmology 76:257 (1992). Although several drugs are currently used or under investigation for such reduction or protection, a need continues to exist for an efficacious method of reducing and/or preventing cataract formation which can readily be used without adverse side effects on humans.

SUMMARY OF THE INVENTION

This need is met by the composition and method according to the subject invention. A composition is provided for reduction of structural changes (defects) in metastable tissue systems. The composition comprises defect-reducing amounts of a structure maker and a physiologically acceptable carrier.

Further in accordance with the subject invention, a method is provided for reducing defects in a metastable tissue system which comprises selecting a metastable tissue system having defects therein, and exposing the system to a structure maker. The structure maker reduces the defects present in the metastable tissue system. Also provided is a method for reducing defects in metastable tissue systems which comprises selecting metastable defect ridden tissue systems, and exposing the system ex situ to a structure maker. Once the structure maker has reduced the structural defects of the metastable tissue system, the autograft may then be returned to its in situ site.

In all cases, the structure maker reduces or eliminates the structural defects and therefore prevents the subsequent formation of further pathology in the metastable tissue system so treated.

As used herein, a metastable tissue system refers to those biological systems which are in disorder. These tissue systems are not in equilibrium and include such systems as the crystalline lens of the eye and any metastable system in which the same cells are present for long periods of time.

Structural defects can occur in the molecules in these systems, which can be detected by measuring the photoluminescence of these tissue systems. [See J. Schroeder, et al., Mat. Res. Symp. Proc. 272:251–263 (1992)]. Photoluminescence is an indicator that microscopic and/or macroscopic defects exist in the ordering of the system, irrespective of whether the system is a solid state system or a biological system. In either type of system, the photoluminescent spectral response of the system provides evidence for the presence or absence (or the mending) of microscopic structural defects within that system.

For example, in the metastable system that comprises the crystalline lens of the eye, an increase in the photoluminescence intensity occurs over time with the magnitude of photoluminescence increasing with age. [See also the confirmation of this effect called autofluorescence (sic) in the work of P. J. Airaksinen et al., Invest. Ophthal. Vis. Sci. 34: 762 (1993 Suppl.)]. Structural defects in the tissue of the lens of the eye are believed to be the precursor modes for formation of cataracts. These structural defects manifest themselves in changes to the photoluminescence response spectrum of the lens.

If plotted as intensity versus wavelength, the photoluminescence spectra exhibits a change in intensity, a broadening of its spectral band width, and a shift in the wavelength of the peak toward longer wavelength with age. Thus, the presence of structural defects that eventuate in a clinical cataract can be detected by measuring the photoluminescence response of the lens and determining its deviation from the norm.

In vitro and in vivo measurements of photoluminescence of a lens and of other thinly-sliced tissue systems can be made using a Raman Spectrometer system comprising an Argon-ion Laser (manufactured by Spectra Physics, Mountain View, Calif.) and a Spex Double Monochromator (manufactured by Spex Industries, Metuchen, N.J.) with subsequent photon counting, detection and stabilization equipment, and a data handling microprocessor also provided by Spex Industries.

Structure makers as used herein refer to ions of very high charge density and very low mass and small ionic radii that can restore order and in turn can affect the degree of devitrification of the metastable system. A structural defect can be viewed as a space or vacancy of microscopic dimensions (molecular or atomic in size) within the structure of the system. The structure maker occupies that space or vacancy to return the structure to a state having the same order as existed before the defect was produced. The degree of order of the system, which relies on the presence or absence of such structural defects, can be severely influenced by the number of these defects. Structure makers are known in the field of aqueous electrolyte solutions to accomplish a similar ordering of the system, and generally include ions smaller and more highly charged than potassium ($K^+$). Such structure makers include, for example, lithium ($Li^+$), fluorine ($F^-$), calcium ($Ca^{2+}$), and the hydroxyl radical ($OH^-$). The compositions of the subject invention utilize the structure makers to reduce and/or mend structural defects. If a structure maker is present in the intermolecular spaces of the tissue when a perturbation results in a structural defect, then the presence of the structure maker causes an immediate restoration of the predefect order in the system. Lithium salts such as lithium chloride and lithium carbonate are preferred because at suitable doses they are well tolerated by humans who can ingest in excess of one gram/day for extended periods of time without significant untoward risk.

BRIEF DESCRIPTION OF THE FIGURES

These features and advantages of this invention will be evident from the following detailed description of preferred embodiments when read in conjunction with the accompanying drawings in which.

DETAILED DESCRIPTION OF THE INVENTION

Figure 1:
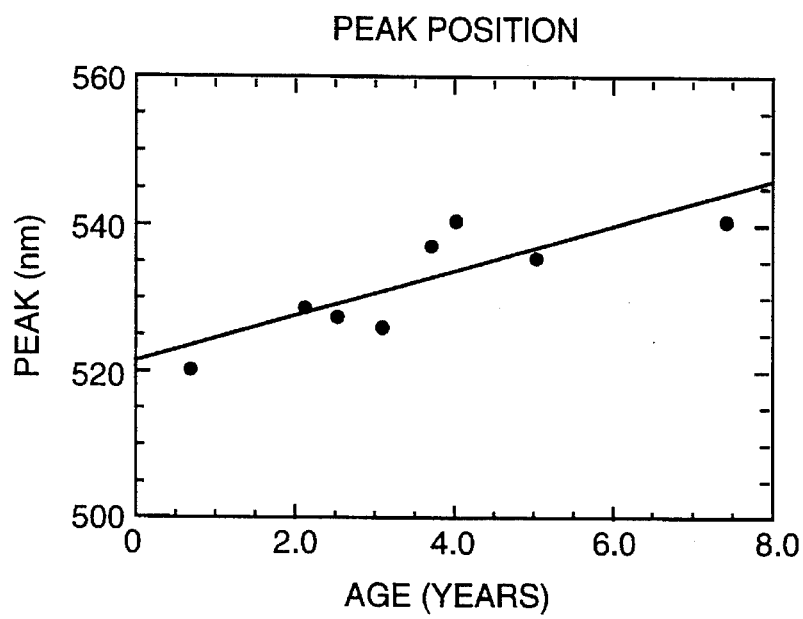
FIG. 1 is a graph showing the red-shift of photoluminescence spectral peak position versus age for eight (8) in vitro human lenses.

This invention teaches that no description of the transmission of electromagnetic waves (light) through biological tissues will be complete without measuring and understanding photoluminescence and absorption, as well as the scattering of the light, in the tissue medium. These three factors, photoluminescence, absorption and scattering, together determine the fate of any electromagnetic wave (ray of light) that passes through any tissue. All three factors change with external perturbations and time (age) in determinable and deterministic ways.

In cataract, photoluminescence, absorption and scattering of electromagnetic waves are elevated relative to age-matched lenses. The elevation can be detected in the retinal plane of the eye by visual tests suitably designed to reflect such elevations. In other biological tissues that are not necessarily completely transparent to visible light but are prepared such that the optical density is sufficiently low (i.e. very thin sections), these same factors can be assessed in in vitro biopsied material with the above-mentioned optical instruments. Again, however, the existence of structural defects and indicators of metastable behavior provide evidence of the tissue changes correlated with other diseases or altered states. The measured magnitudes of these three factors in all cases are determined by the nano-structural (mesoscopic) details of the tissue, namely, the defects or nano-inhomogeneities that exist in the molecular make-up of the tissue.

In those molecular cell components of biological systems that exhibit properties found in metastable systems, and also in systems exhibiting defects (as determined by their response to optical excitation), the incidence of defect migration and subsequent folding and multiplication can be inhibited by the incorporation of certain classes of ions into these tissues. These classes of ions are generally grouped under the generic term of "structure makers". In general, the structure makers will consist of ions of small ionic radii and well-defined high charge densities, for example lithium ions. Although this analysis is particularly appropriate to the human crystalline lens and the formation of senile cataracts, it is not limited to this system only and applies to any other metastable tissue system as well.

The mechanisms of the structural changes and the eventual devitrification process leading to senile cataract formation are similar to those that exist in a solid solution. Over time the process is initially on a microscopic scale (i.e., dimensions of several nanometers). However, with further degradation, macroscopic dimensions are achieved (i.e., micron size) with the consequent onset of a pathological state (as exhibited by the changes in the transparency that occur in the cataractous lens which manifests itself in increased scatter, photoluminescence and absorption). However, this same analysis applies to any other biological system that exhibits such defects, or vacancies, in combination with metastability.

Measurements have shown, for example, that in vitro lenses immersed in a physiological saline (NaCl) solution, 20% of which is LiCl, a structure maker, brings about beneficial changes in these human lenses as exhibited by precise optical measurements. These changes can be interpreted as a reversal of the normal aging process of the lens. The data for treatment with a non-structure maker (KCl) when comprising 20% of a physiological saline show no comparable beneficial effect. These results are given in Table 1. Eyes from the same donor were employed in the comparison of the structure maker to non-structure maker, i.e., one eye of the donor was exposed to the structure maker, LiCl, while the opposite eye was exposed to the non-structure maker, KCl.

Referring to FIG. 1, the substantially linear increase of the position of the photoluminescent peak of lenses by age is shown. The linear progression establishes that as the lens ages, a shift to longer wavelengths (i.e. red-shift) in peak position occurs which is indicative of an increase in structural defects within the lens system.

Figure 2:
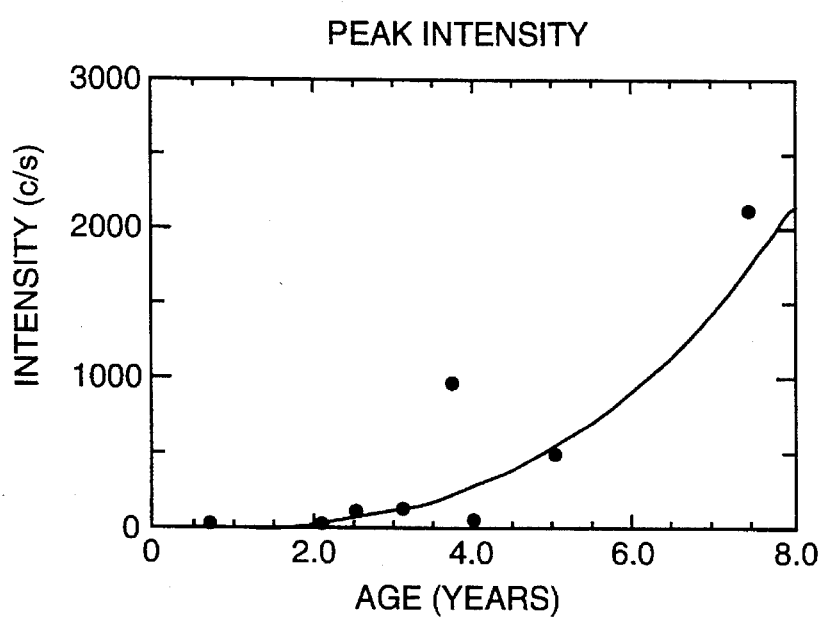
FIG. 2 is a graph showing photoluminescence peak intensity versus age for the same set of human lenses as shown in FIG. 1.

Referring to FIG. 2, the intensity of the peak photoluminescence is plotted as a function of age, again showing an increase over time. If log of intensity were plotted, a linear progression would be seen, establishing that as the lens gets older, an increase in peak intensity occurs which is also indicative of an increase in structural defects within the lens system.

Figure 3:
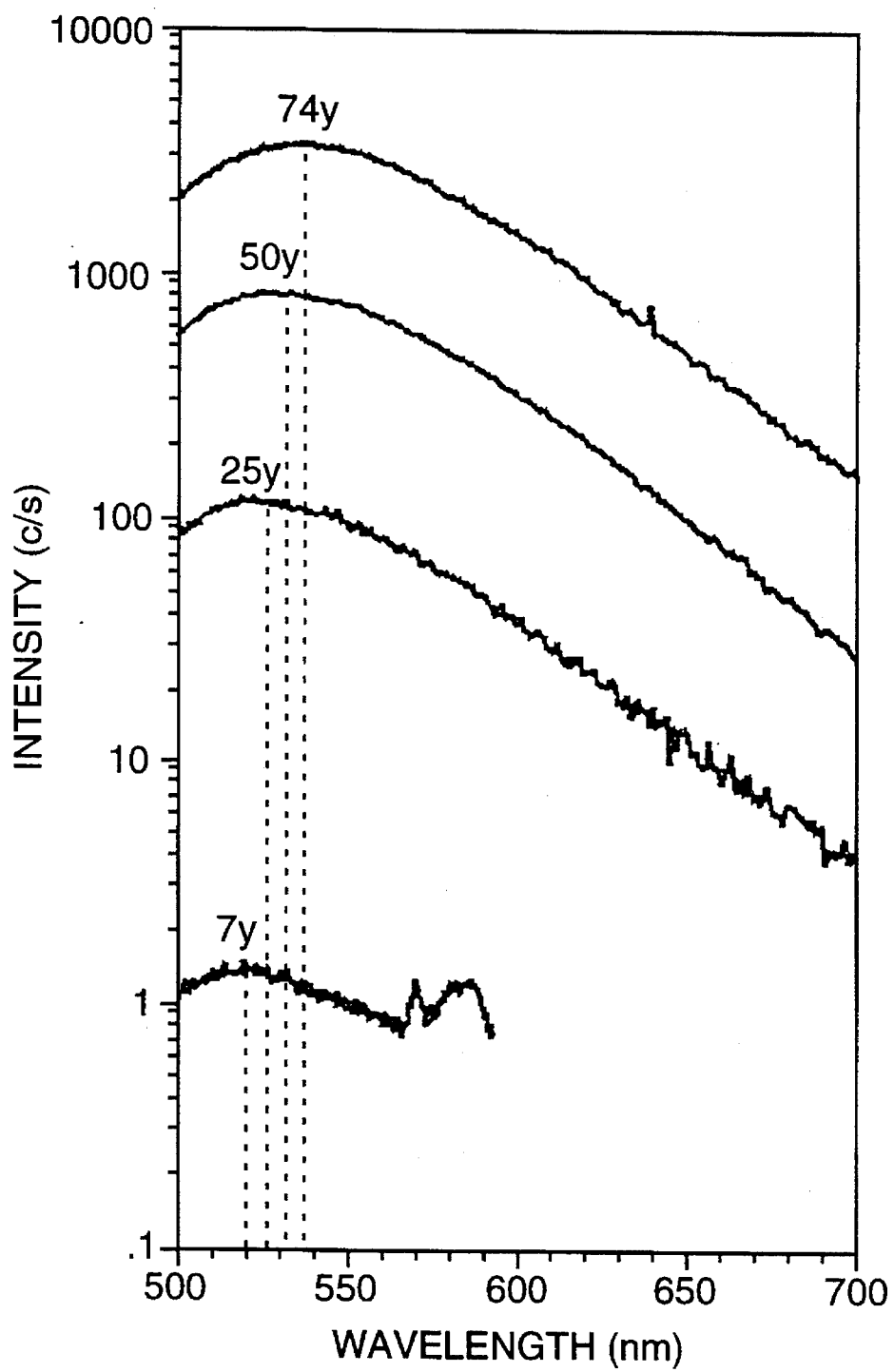
FIG. 3 is a graph showing photoluminescence intensity versus wavelength for four (4) in vitro human lenses.
Figure 1:
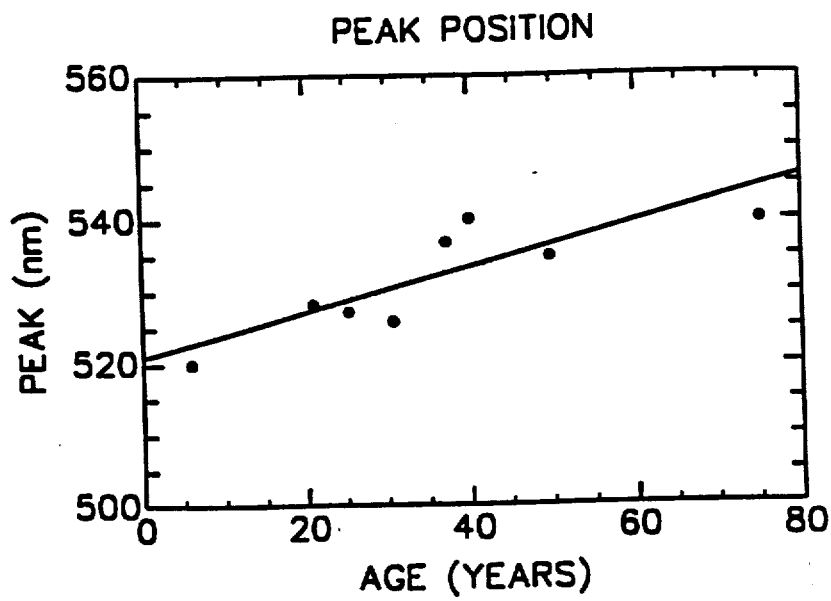
Figure 2:
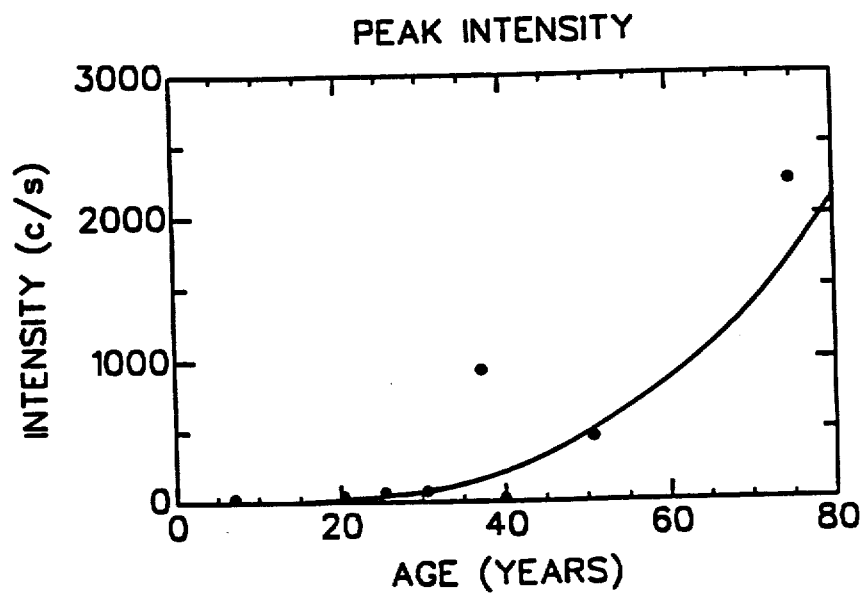

FIG. 3 shows the photoluminescence intensity plotted against wavelength for four human donor lenses of various ages (74 years, 50 years, 25 years, and 7 years). The exciting wavelength is 488 nm. Note that as defects increase in the lenses due to the increasing age of the donor, there is an increase in the peak intensity, a broadening of the spectral band (i.e., the full width of the peak at half maximum photoluminescence intensity), and a shift in the wavelength of the peak. These three changes are characteristic of the presence of increasing structural defects within these systems. This analysis is supported by similar spectral behavior in a glass, a disordered solid system, where the three spectral properties of photoluminescence, absorption and scattering change similarly as structural defects increase and the solids become more devitrified. [See J. Schroeder, Light Scattering of Glass. Treatise on Materials Science and Technology, Vol. 12, Glass 1: Interaction with Electromagnetic Radiation (1977), pp. 157–222, Academic Press Inc., New York; and J. Schroeder et al., Mat. Res. Soc. Symp. Proc. 272:251–263 (1992)].

The effect of the structure makers on these characteristic age changes of the human lens was determined by immersing one each of a matched pair of lenses for at least one hour at room temperature in a physiological saline solution (NaCl), 20% of which consisted of isomolar lithium chloride (LiCl) or isomolar potassium chloride (KCl). The results of these tests are shown in Table 1. With lithium ion treatment, the shift of the peak position to a longer wavelength is reversed, i.e. the mean peak wavelength before treatment was 532.4 nm, and the mean position after treatment with a structure maker was 527.9 nm. This decrease in the mean peak position (−4.5 nm shift) is indicative of a reduction in the number of structural defects as discussed above and is equivalent in both donors to the number of structural defects that would accumulate in a fourteen year period.

When a non-structure maker bath is used, the mean shift is only −0.6 nm. Thus it is clear that structure makers such as lithium salts are able to alter the structural defects of the lens and produce a blue-shift in the peak of the photoluminescence spectrum. These observations of in vitro human donor lenses treated with lithium ions are consistent with the protection afforded against selenium induced cataracts in Wistar suckling rats. [X. R. Huang, et al., Invest. Ophthal. Vis. Sci. 34:1064 (1993 Suppl.)]. Note moreover that selenium ions are classified as structure breakers and consequently produce structural defects leading to cataractogenesis.

As discussed above, the in vitro donor lenses were exposed to lithium ions by immersion in a solution containing lithium salts. The lithium ions could also be administered in vivo in the form of eye drops which would permit a smaller total dose to be more localized to the crystalline lens. Moreover, diffusion of the lithium ions to the lens or other tissue could be facilitated by iontophoresis, the small diameter of the lithium ions lending itself admirably to this route of entry. If confined to this route of entry, 30 mg of LiCl/day in an isomolar physiological saline carrier provides an efficacious dose. However, where a systemic route must be employed, larger daily doses will require dosages on the order of 750 mg/day. Still higher concentrations may be employed with autografts, however the excess structure makers would be removed before the tissue was replaced.

This data shows that lithium salts, identified as structure makers, are an effective treatment for lenticular structural defect management in which there is an increased photoluminescence, absorption and scattering in any tissue in which structural defects and metastable properties coexist.

In summary this invention teaches that ions identified as structure makers are an effective means to alter opacifying structural defects in metastable tissue systems in which there is an increased photoluminescence, absorption and scatter resulting from disorder in the nanostructural matrix.

TABLE 1

| | Blueshift in the Peak Photoluminescence Values With Treatment | |
|---|---|---|
| | 20% Li$^+$ | 20% K$^+$ |
| before treatment* | $v_{1,1}$ = 526.7 nm $v_{1,2}$ = 538.0 nm | $v_{1,1}$ = 526.2 nm $v_{1,2}$ = 537.0 nm |
| after treatment* | $v_{1,1}$ = 522.4 nm $v_{1,2}$ = 533.3 nm | $v_{1,1}$ = 525.2 nm $v_{1,2}$ = 536.8 nm |
| variation due to treatment | $\Delta_1$ = −4.3 nm $\Delta_2$ = −4.7 nm | $\Delta_1$ = −1.0 nm $\Delta_2$ = −0.2 nm |

*treatment consists of immersion for at least one hour at room temperature in isotonic saline solution (NaCl) 20% of which consists of isomolar lithium chloride, or potassium chloride Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined by the following claims.

What is claimed is:

1. A method of reducing eventual opacification in a human lens by reducing structural defects in a precursor mode, said method comprising:

selecting an intact human lens having structural defects that are precursors to opacification therein; and exposing said human lens to an amount of a structure maker sufficient to reduce structural defects in said precursor modes, said structure maker selected from the group consisting of lithium salts, fluoride salts, calcium salts, and sources of hydroxide (OH$^-$), said structure maker reducing said structural defects that eventuate in opacification in said lens.

2. The method of claim 1 wherein said structure maker is lithium chloride or lithium carbonate.

3. The method of claim 1 wherein said structure maker is introduced into said human lens by iontophoresis.

4. The method of claim 1 wherein said structure maker is introduced into said human lens by topical application of a solution.

* * * * *

UNITED STATES PATENT AND TRADEMARK OFFICE
CERTIFICATE OF CORRECTION

PATENT NO. : 5,516,534

DATED : May 14, 1996

INVENTOR(S) : Schroeder et al.

It is certified that errors appear on the drawings in the above-identified patent and that said Letters Patent is hereby corrected as shown below:

Delete Drawing sheet 1 of 2 and substitute therefor the Drawing sheet, consisting of Figs. 1-2, as shown on the attached page.

Signed and Sealed this

Third Day of December, 1996

Attest:

BRUCE LEHMAN

Attesting Officer

Commissioner of Patents and Trademarks